United States Patent [19]

Nakano et al.

[11] Patent Number: 4,966,774

[45] Date of Patent: Oct. 30, 1990

[54] SUPEROXIDE DISMUTASE COMPOSITION

[75] Inventors: Michinobu Nakano, Ageo; Kazuo Katoh, Kobe, both of Japan

[73] Assignee: Nippon Kayaku Kabushiki Kaisha, Tokyo, Japan

[21] Appl. No.: 369,300

[22] Filed: Jun. 21, 1989

[30] Foreign Application Priority Data

Jul. 12, 1988 [JP] Japan .................................. 63-171794

[51] Int. Cl.$^5$ ...................... A61K 33/42; A61K 33/14; A61K 31/70; A61K 35/50
[52] U.S. Cl. .................................... 424/601; 424/663; 514/6; 514/7; 514/23
[58] Field of Search ..................... 424/601, 663; 514/6, 514/7, 23

[56] References Cited

U.S. PATENT DOCUMENTS

| | | | |
|---|---|---|---|
| 868,566 | 10/1907 | Hughes | 424/101 |
| 3,133,001 | 5/1964 | Muset | 514/23 |
| 4,842,846 | 6/1989 | Nakano | 514/900 |

FOREIGN PATENT DOCUMENTS 0246569 5/1987 European Pat. Off. .
0273579 11/1987 European Pat. Off. .

OTHER PUBLICATIONS

Strothkamp, et al., JACS, 1982, 104, 852–853.
The World Biotech Report, 1984, vol. 1: Europe, pp. 379–390.
Chemical Abstracts, vol. 96, 1982, No. 9, Mar. 1, Abstract No. 64823K.

*Primary Examiner*—Mukund J. Shah
*Assistant Examiner*—E. C. Ward
*Attorney, Agent, or Firm*—Henry C. Nields

[57] ABSTRACT

A stable SOD composition comprising superoxide dismutase (SOD), a phosphate, an alkali metal chloride and sucrose is disclosed.

2 Claims, No Drawings

SUPEROXIDE DISMUTASE COMPOSITION

BACKGROUND OF THE INVENTION

The superoxide dismutase, which will be referred to as SOD hereinafter, composition of the present invention is valuable in the prevention and treatment of tissue disorders caused by superoxides.

Namely, it may be employed as, for example, an antiinflammatory agent or a remedy for ischemic cardiac diseases.

A preparation of SOD extracted from bovine liver has been already marketed in Western Germany as a remedy for, e.g., rheumatoid arthritis.

Although this preparation is a valuable medicine, it is accompanied by a problem in that it shows an antigenicity when administered to man since it originates from bovine. In order to overcome this problem, it has been recently attempted to produce SOD originating from human on a large scale through genetic recombination techniques (cf. EP-A1-180964 and EP-A1-173280). However these purified SODs thus obtained, in particular human Cu-Zn SOD, are poor in stability.

SUMMARY OF THE INVENTION

A highly purified SOD is unstable and has some problems in that it is liable to be inactivated when formulated into a lyophilized powder or when stored in the form of, for example, an aqueous solution or a powder, and that it would suffer from clouding caused by polymerization.

Accordingly, it is on object of the present invention to provide a stable SOD composition.

As a result of intensive studies, the present inventors have found that a phosphate such as sodium phosphate and an alkali metal chloride such as sodium chloride are effective in stabilizing a highly pure SOD and that the combined use of sucrose therewith would give a stable SOD composition scarcely suffering from any decrease in the activity or denaturation caused by, for example, polymerization, thus completing the present invention.

DETAILED DESCRIPTION OF THE INVENTION

The present invention relates to an SOD composition comprising a phosphate, an alkali metal chloride and sucrose.

The SOD to be used in the present invention may be any of the Cu-Zn type, Fe type and Mn type of SOD.

Among them, a Cu-Zn SOD originating from plants such as spinach or a Mn SOD originating from bacteria such as *Escherichia coli* may also be used.

Further the abovementioned types of SODs prepared through genetic recombination techniques may also be employed.

The present invention is particularly useful for human Cu-Zn SOD, still particularly, a recombinant SOD produced by, for example, recombinant *E. coli.* Human Cu-Zn SOD is particularly preferable from the viewpoint of clinical administration to man.

Examples of the alkali metal chloride to be used in the present invention include sodium chloride and potassium chloride, among which sodium chloride is usually employed.

In the present invention, any phosphate may be used so long as it is pharmacologically acceptable. Alkaline metal phosphates, in particular sodium phosphate, are preferable.

The amounts of the components of the SOD composition of the present invention may vary widely without any restriction, so long as the SOD can be stabilized thereby.

For example, the phosphate may be used in an amount of about 0.05 $\mu$mol or above, preferably about 0.1 to about 20 $\mu$mol and still preferably about 0.3 to about 4 $\mu$mol; the alkali metal chloride may be employed in an amount of about 0.05 mg or above, preferably about 0.1 to about 50 mg and still preferably about 0.1 to about 25 mg; and sucrose may be employed in an amount of about 1 mg or above and preferably about 3 mg or above, each per 100,000 U of the SOD. Although the uppler limit of the sucrose content is not particularly specified, it is preferably used in an amount not exceeding about 150 mg from the practical viewpoint. Still preferably, the sucrose may be used in an amount of about 7 to about 60 mg.

The SOD composition of the present invention may be formulated into, for example, oral preparations, injections or external preparations optionally together with, for example, fillers or adjuvants.

These fillers and adjuvants may be selected from among those conventionally used in the art depending on the purpose. Examples thereof include water, sugars, sugar alcohols, amino acids, proteins and inorganic salts. The amount of these additives is not particularly restricted. They may be usually added in an amount of 0 to about 5 g, preferably 0 to about 2 g, per 100,000 U of the SOD.

Therefore the SOD composition of the present invention has the following composition per 100,000 U of the SOD protein:

| | |
|---|---|
| SOD protein | 100,000 U, |
| alkali metal chloride | ca. 0.05–ca. 50 mg, |
| phosphate | ca. 0.05–ca. 20 $\mu$mol (as phosphoric acid), |
| sucrose | ca. 1 to ca. 150 mg, and |
| other additives | 0 to 5 g, (e.g., fillers or adjuvants) |

The SOD composition of the present invention may be prepared by, for example, the following method.

When a highly purified SOD is to be employed, the SOD, an alkali metal chloride, preferably sodium chloride, and sucrose are dissolved in a solution such as a phosphate buffer in an arbitrary order. Thus the SOD composition of the present invention is obtained in the form of an aqueous solution. This aqueous solution may be further lyophilized to thereby give the SOD composition of the present invention in the form of a powder.

When the SOD to be used contains an alkali metal chloride such as sodium chloride originating from the preparation process, an additional alkali metal chloride may be added thereto, if required. Then sucrose is added thereto and the obtained mixture is dissolved in a phosphate buffer, optionally followed by lyophilization.

When a chromatographic treatment with the use of, for example, a Sephadex column is to be used in the final step of the preparation of the SOD, the resin has been preliminarily equilibrated with a phosphate buffer containing an alkali metal chloride and having a pH value of about 5.0 to 9, preferably about 5.5 to 8. Then the SOD is adsorbed on the column and eluted with the same phosphate buffer. Subsequently sucrose is added to the eluate to thereby give the SOD composition of the present invention in the form of an aqueous solution. Alternately, the eluate is lyophilized, either as such or after being concentrated, and then sucrose is added thereto. The obtained mixture is dissolved in water to thereby give the SOD composition of the present invention. The obtained aqueous solution may be further lyophilized to thereby give a powder, if desired.

Alternately, when a phosphate buffer is not employed, the addition of the phosphate may be conducted in the following manner. Namely, a phosphate such as an alkali metal phosphate, an alkali metal monohydrogen phosphate or an alkali metal dihydrogen phosphate is added to the SOD together with sucrose to give an aqueous solution, which may be then optionally lyophilized. The lyophilization is made by a usual method, for example, as follows:

The aqueous solution containing about 5% by weight to about 50% by weight in total amount of SOD, alkali metal chlorides, phosphates, sucrose and if necessary, further other additives is freezed at below about $-20°$ C. to about $-200°$ C., usually below $-30°$ C. to $-80°$ C. and dried under reduced pressure below 10 torr (=mmHg) usually below 1 torr, preferably below 0.1 torr.

The activity of the SOD to be used in the present invention is determined by the xanthine-xanthine oxidase method reported by McCord and Fridovich (cf. J. Biol., Chem., 244, 6049 (1969)). Effect:

(1) Test method

A powdery sample is stored in the dark at 65° C. for two weeks while a change in the SOD activity is monitored and the amount of the aggregated SOD formed through denaturation is determined. A sample in the form of an aqueous solution is stored at room temperature under irradiating at 1000 lx for two weeks while a change in the SOD activity is monitored and the amount of the aggregated SOD is determined.

(2) Preparation of specimen

As the specimen, a known h-SOD obtained by genetic recombination techniques which is highly pure and thus substantially free from any salt is employed. An aqueous solution of a specimen (control) is prepared by dissolving 700,000 U of said highly pure h-SOD in distilled water, adjusting the pH value to 7 and adjusting the total volume to 10 ml.

A specimen of the SOD composition of the present invention is prepared by dissolving 700,000 U of said highly pure h-SOD and 150 mg of sucrose in a 0.5 mM sodium phosphate buffer containing 1 mg/ml of sodium chloride, adjusting the pH value of the obtained solution to 7 and adjusting the total volume thereof to 10 ml.

Further an aqueous solution obtained in the same manner as the one described above is lyophilized to thereby give lyophilized powdery specimen. Table 1 shows the composition of each specimen.

TABLE 1

| Specimen | Composition of specimen Composition |
|---|---|
| Control | SOD: 700,000 U |
| Invention | SOD: 700,000 U, sucrose: 150 mg, sodium phosphate: 0.6 mg (5 μmol), NaCl: 10 mg |

(3) Result

Table 2 shows the results.

TABLE 2

| | Stability of SOD composition | | |
|---|---|---|---|
| | Powder | | Aqueous solution |
| Specimen | Activity % | Gel filtration | Gel filtration |
| Control | 71% | 6.4% | 7.2% |
| Invention | 101% | 0% | 0% |

In the above Table 2, the activity data are expressed each in the ratio (%) to the initial activity while the gel filtration data show each the content (%) of the aggregation SOD. At the initiation, no aggregation SOD is present (0%).

Therefore the combined use of the phosphate, sodium chloride and sucrose completely inhibits the formation of the aggregation SOD without lowering the activity thereof.

These results obviously indicate that the composition of the present invention has a remarkably elevated SOD stability as compared with the control.

EXAMPLE 1

100,000 U of a highly pure h-SOD and 30 mg of sucrose were dissolved in 10 ml of a 0.5 mM phosphate buffer containing 5 mg of sodium chloride. The obtained solution was lyophilized to thereby give the SOD composition of the present invention having the following composition:

| SOD | 100,000 U, |
|---|---|
| sodium phosphate | 5 μmol, |
| sodium chloride | 5 mg, and |
| sucrose | 30 mg. |

EXAMPLE 2

The SOD composition of the following composition was prepared according to the abovementioned process:

| SOD | 300,000 U, |
|---|---|
| sodium phosphate | 5 μmol, |
| sodium chloride | 10 mg, and |
| sucrose | 150 mg. |

EXAMPLE 3

The SOD composition of the following composition as prepared according to the abovementioned process:

| SOD | 100,000 U, |
|---|---|
| sodium phosphate | 10 μmol, |
| sodium chloride | 30 mg, and |
| sucrose | 150 mg. |

EXAMPLE 4

A lyophilized SOD powder having the following composition was prepared:

| SOD | 700,000 U, |
|---|---|
| sodium phosphate | 5 μmol, and |

| | |
|---|---|
| sodium chose | 10 mg. |

200 mg of sucrose was added thereto and the obtained mixture was dissolved in 10 ml of distilled water. The pH value of the solution was adjusted to 6.5. After filtration and sterilization, 5 ml of the solution was filled in a vial and lyophilized to thereby give a lyophilized preparation.

We claim:

1. A superoxide dismutase (SOD) composition the following components:

| | |
|---|---|
| SOD protein | 100,000 U, |
| alkali metal chloride | ca. 0.05 to ca. 50 mg, |
| phosphate | ca. 0.05 to ca. 20 μmol (as phosphoric acid), and |
| sucrose | ca. 1 to ca. 150 mg, | together with 0 to about 5 g of other additives such as filters or adjuvants.

2. An SOD composition as set forth in claim 1 comprising the following components:

| | |
|---|---|
| human Cu—Zn SOD | 100,000 U, |
| alkali metal chloride | ca. 0.1 to ca. 25 mg, |
| alkali metal phosphate | ca. 0.3 to ca. 4 μmol, |
| sucrose | ca. 7 to ca. 60 mg. |

* * * * *